United States Patent
Andaya et al.

(10) Patent No.: US 11,013,192 B2
(45) Date of Patent: May 25, 2021

(54) RICE CULTIVAR M-211

(71) Applicant: CALIFORNIA COOPERATIVE RICE RESEARCH FOUNDATION, INC., Biggs, CA (US)

(72) Inventors: Virgilio Cedro Andaya, Chico, CA (US); Teresa Bermejo De Leon, Chico, CA (US); Shyamal Krishna Talukder, Chico, CA (US); Cynthia Bato Andaya, Chico, CA (US); Kent Scheidel McKenzie, Oroville, CA (US)

(73) Assignee: California Cooperative Rice Research Foundation, Inc., Biggs, CA (US)

( * ) Notice: Subject to any disclaimer, the term of this patent is extended or adjusted under 35 U.S.C. 154(b) by 0 days.

(21) Appl. No.: 17/123,329

(22) Filed: Dec. 16, 2020

(65) Prior Publication Data
US 2021/0100192 A1 Apr. 8, 2021

(51) Int. Cl.
*A01H 5/10* (2018.01)
*A01H 6/46* (2018.01)

(52) U.S. Cl.
CPC ............ *A01H 6/4636* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,492,582 B2 | 12/2002 | Johnson | |
| 6,911,589 B2 | 6/2005 | Johnson | |
| 6,956,154 B2 | 10/2005 | Xie | |
| 7,301,083 B2 | 11/2007 | Sarreal et al. | |
| 8,841,526 B2 * | 9/2014 | Linscombe | A01H 5/10 800/320.2 |
| 9,693,520 B1 | 7/2017 | Andaya et al. | |

OTHER PUBLICATIONS

Allard, R.W., 1999, Breeding Self-Pollinated Plants, Principles of Plant Breeding, 2$^{nd}$ ed., John Wiley & Sons, Inc., pp. 175-197.
Altpeter, F., et al., 2016, Advancing Crop Transformation in the Era of Genome Editing, *The Plant Cell*, 28:1510-1520.
Bennetzen, et al., 1992, Approaches and progress in the molecular cloning of plant disease resistance genes, *Genetic Engineering*, 14:99-124.
DeBolle, et al., 1996, Antimicrobial peptides from *Mirabilis jalapa* and *Amaranthus caudatus*: expression, processing, localization and biological activity in transgenic tobacco, *Plant Molec. Biol.*, 31:993-1008.
Eshed, et al., 1996, Less-than-additive epistatic interactions of quantitative trait loci in tomato, *Genetics*, 143:1807-1817.
Hill, et al., 2014, Agronomy Progress Report, California Rice Varieties, UCDavis Plant Sciences, No. 317, 27 pages.
Hill, et al., 2015, Agronomy Progress Report, California Rice Varieties, UCDavis Plant Sciences, No. 319, 25 pages.
Jiang, G.L., 2013, Molecular Markers and Marker-Assisted Breeding in Plants, Plant Breeding from Laboratories to Fields, InTech, pp. 45-83.
Kamburova, V.S., et al., 2017, Genome Editing in Plants: An Overview of Tools and Applications, *Intl J. of Agronomy*, Article ID 7315351, 15 pages.
Kraft, et al., 2000, Linkage disequilibrium and fingerprinting in sugar beet, *Theor. Appl. Genet.*, 101:323-326.
Linquist, et al., 2016, Agronomy Progress Report, California Rice Varieties, UCDavis Plant Sciences, No. 321, 25 pages.
Linquist, et al., 2017, Agronomy Progress Report, California Rice Varieties, UCDavis Plant Sciences, No. 324, 26 pages.
Linquist, et al., 2018, Agronomy Progress Report, California Rice Varieties, UCDavis Plant Sciences, No. 325, 25 pages.
Linquist, et al., 2019, Agronomy Progress Report, California Rice Varieties, UCDavis Plant Sciences, No. 327, 25 pages.
Linquist, et al., 2020, Agronomy Progress Report, California Rice Varieties, UCDavis Plant Sciences, No. 328, 25 pages.
Malzahn, A., et al., 2017, Plant genome editing with TALEN and CRISPR, *Cell Biosci*, 7:21, 18 pages.
McKenzie, et al., 1994, Breeding improved rice cultivars for temperate regions: a case study, *Australian Journal of Experimental Agriculture*, 34:897-905.
Palmer, J., 2018, Letter to Cooperative Extension Rice Farm Advisors and California Certified Rice Seed Applicants and Growers, 2 pages.
Pang, et al., 1992, Expression of a gene encoding a scorpion insectotoxin peptide in yeast, bacteria and plants, *Gene*, 116:165-172.
Poehlman, J.M. and Sleper, D.A., 1995, Breeding Field Crops, 4th Ed., Iowa State University Press, p. 473.
Smith, C.W. and Dilday, R.H., 2003, Origin, Domestication, and Diversification in Rice: Origin, History, Technology, and Production, John Wiley & Sons, Inc., pp. 4-6.
Yu, et al., 1997, Importance of epistasis as the genetic basis of heterosis in an elite rice hybrid, *Proc. Natl. Acad. Sci.*, 94:9226-9231.

* cited by examiner

*Primary Examiner* — Medina A Ibrahim
(74) *Attorney, Agent, or Firm* — Jondle & Associates, P.C.

(57) ABSTRACT

A rice cultivar designated M-211 is disclosed. The invention relates to the seeds of rice cultivar M-211, to the plants of rice M-211 and to methods for producing a rice plant produced by crossing the cultivar M-211 with itself or another rice variety. The invention further relates to methods for producing a rice plant containing in its genetic material one or more transgenes and to the transgenic rice plants and plant parts produced by those methods. This invention also relates to rice cultivars or breeding cultivars and plant parts derived from rice cultivar M-211, to methods for producing other rice cultivars, lines or plant parts derived from rice cultivar M-211 and to the rice plants, varieties, and their parts derived from the use of those methods. The invention further relates to hybrid rice seeds and plants produced by crossing the cultivar M-211 with another rice cultivar.

28 Claims, No Drawings

RICE CULTIVAR M-211

BACKGROUND OF THE INVENTION

The present invention relates to a new and distinctive rice cultivar designated M-211. All publications cited in this application are herein incorporated by reference.

Rice is an ancient agricultural crop and is today one of the principal food crops of the world. There are two cultivated species of rice: Oryza sativa L., the Asian rice, and O. glaberrima Steud., the African rice. O. sativa L. constitutes virtually all of the world's cultivated rice and is the species grown in the United States. Three major rice producing regions exist in the United States: the Mississippi Delta (Arkansas, Miss., northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. For the dry-seeded system, when the plants have reached sufficient size (four- to five-leaf stage), a shallow permanent flood of water 5 to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium-grain, and short-grain. Typical U. S. long-grain cultivars cook dry and fluffy when steamed or boiled, whereas medium- and short-grain cultivars cook moist and sticky. Long-grain cultivars have been traditionally grown in the southern states and generally receive higher market prices.

Rice, Oryza sativa L., is an important and valuable field crop. Thus, a continuing goal of plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel rice cultivar designated M-211. This invention thus relates to the seeds of rice cultivar M-211, to the plants of rice M-211 and to methods for producing a rice plant produced by crossing the rice M-211 with itself or another rice line, to methods for producing a rice plant containing in its genetic material one or more transgenes and to the transgenic rice plants produced by that method, and the creation of variants by mutagenesis or transformation of rice cultivar M-211. The present invention relates to rice plants having essentially all of the physiological and morphological characteristics of rice cultivar M-211. This invention also relates to methods for producing other rice cultivars derived from rice cultivar M-211 and to the rice cultivar derived by the use of those methods. This invention further relates to hybrid rice seeds and plants produced by crossing cultivar M-211 with another rice cultivar.

Thus, any such methods using the rice cultivar M-211 are part of this invention: selfing, backcrosses, hybrid production, crosses to populations, and the like. All plants produced using rice variety M-211 as a parent are within the scope of this invention. Advantageously, the rice variety could be used in crosses with other, different rice plants to produce first generation ($F_1$) rice hybrid seeds and plants with superior characteristics.

In another aspect, the present invention provides protoplasts and regenerable cells for use in tissue culture of rice plant M-211. The tissue culture will preferably be capable of regenerating plants having the physiological and morphological characteristics of the foregoing rice plant and of regenerating plants having substantially the same genotype as the foregoing rice plant. Preferably, the regenerable cells in such tissue cultures will be embryos, protoplasts, meristematic cells, callus, pollen, leaves, anthers, root tips, flowers, seeds, panicles or stems. Still further, the present invention provides rice plants regenerated from the tissue cultures of the invention.

In another aspect, the present invention provides for single or multiple gene converted plants of M-211. The single or multiple transferred gene(s) may preferably be a dominant or recessive allele. Preferably, the single or multiple transferred gene(s) will confer such traits as herbicide resistance, insect resistance, resistance for bacterial, fungal, or viral disease, male fertility, male sterility, enhanced nutritional quality, and industrial usage. The single or multiple gene(s) may be a naturally occurring rice gene or a transgene introduced through genetic engineering techniques. The invention also relates to methods for producing a rice plant containing in its genetic material one or more transgenes and to the transgenic rice plant produced by that method.

In another aspect, the present invention provides for methods of introducing one or more desired trait(s) into the rice line M-211 and plants or seeds obtained from such methods. The desired trait(s) may be, but not exclusively, a single gene, preferably a dominant but also a recessive allele. Preferably, the transferred gene or genes will confer such traits as male sterility, herbicide resistance, insect resistance, disease resistance, resistance for bacterial, fungal, or viral disease, male fertility, water stress tolerance, enhanced nutritional quality, modified protein content, enhanced plant quality, enhanced digestibility and industrial usage. The gene or genes may be naturally occurring rice gene(s). The method for introducing the desired trait(s) may be a backcrossing process making use of a series of backcrosses to the rice cultivar M-211 during which the desired trait(s) is maintained by selection. The desired trait may also be introduced via transformation.

The invention further relates to methods for genetically modifying a rice plant of the rice cultivar M-211 and to the modified rice plant produced by those methods. The genetic modification methods may include, but are not limited to, mutation, genome editing, gene silencing, RNA interference, backcross conversion, genetic transformation, single and multiple gene conversion, and/or direct gene transfer.

The invention further provides methods for developing rice plants in a rice plant breeding program using plant breeding techniques including recurrent selection, backcrossing, pedigree breeding, restriction fragment length polymorphism enhanced selection, genetic marker enhanced selection and transformation. Seeds, rice plants, and parts thereof, produced by such breeding methods are also part of the invention.

Still yet another aspect of the invention is a method of producing a rice plant derived from the rice cultivar M-211, the method comprising the steps of: (a) preparing a progeny plant derived from rice cultivar M-211 by crossing a plant of the rice cultivar M-211 with a second rice plant; and (b) crossing the progeny plant with itself or a second plant to produce a progeny plant of a subsequent generation which is derived from a plant of the rice cultivar M-211. In one embodiment of the invention, the method further comprises: (c) crossing the progeny plant of a subsequent generation with itself or a second plant; and (d) repeating steps (b) and (c) for, in some embodiments, at least 1, 2, 3, 4 or more additional generations to produce an inbred rice plant derived from the rice cultivar M-211. Also provided by the invention is a plant produced by this and the other methods of the invention.

In another embodiment of the invention, the method of producing a rice plant derived from rice cultivar M-211 further comprises crossing the inbred rice plant derived from rice cultivar M-211 with a plant of a different genotype to produce a seed of a hybrid rice plant derived from rice cultivar M-211.

Another embodiment of the invention is a method of introducing the head rice stability trait of rice cultivar M-211 into another rice cultivar by crossing M-211 with a plant of another rice cultivar and selecting for progeny plants that have head rice stability.

In addition to the exemplary aspects and embodiments described above, further aspects and embodiments will become apparent by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Aggregate sheath spot. Is caused by the fungus *Rhizoctonia oryzae-sativae* (Sawada) Mordue (=*Ceratobasidium oryzae-sativae*). This disease causes sheath lesions and can reduce yield and grain quality. California varieties generally rate between 2 and 4 in greenhouse tests on a scale of 0 to 4.

Alkali spreading value. Indicator of gelatinization temperature and an index that measures the extent of disintegration of milled rice kernel in contact with dilute alkali solution. Standard long grains have 3 to 5 Alkali Spreading Value (intermediate gelatinization temperature). Standard medium and short grain rice have 6 to 7 Alkali Spreading Values (low gelatinization temperature).

Allele. Allele is any of one or more alternative forms of a gene, all of which alleles relate to one trait or characteristic. In a diploid cell or organism, the two alleles of a given gene occupy corresponding loci on a pair of homologous chromosomes.

Alter. The utilization of up-regulation, down-regulation, or gene silencing.

Apparent amylose percent. The most important grain characteristic that describes cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grain rice contain 16 to 19% amylose. Waxy rice contains 0% amylose. Amylose values will vary over environments.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bakanae. Is caused by the fungus *Fusarium fujikuroi* Nirenberg (=*Gibberella fujikuroi*). It causes reduced seed germination and abnormal seedling elongation often followed by crown rot. Susceptibility of varieties is expressed as percent symptomatic plants.

Blanking %. Visual estimate of the percent of sterile florets (florets that are empty with no filled kernels) in the panicle as a measurement of cool temperature induced pollen sterility. Blanking may also be induced by high temperatures and by genetic incompatibility of the parents. This data may be collected in screening nurseries at cool locations, cool years, and also in screening tests in refrigerated greenhouses.

Breakdown. The peak viscosity minus the hot paste viscosity.

Breeding. The genetic manipulation of living organisms.

Cell. Cell as used herein includes a plant cell, whether isolated, in tissue culture or incorporated in a plant or plant part.

Cross-pollination. Fertilization by the union of two gametes from different plants.

Cool paste viscosity. Viscosity measure of rice flour/water slurry after being heated to 95EC and uniformly cooled to 50EC (American Association of Cereal Chemist). Values less than 200 for cool paste indicate softer cooking types of rice.

Days to 50% heading. Average number of days from planting to the day when 50% of all panicles are exerted at least partially through the leaf sheath. A measure of maturity.

Diploid. A cell or organism having two sets of chromosomes.

Elongation. Cooked kernel elongation is the ratio of the cooked kernel length divided by the uncooked kernel length. Extreme cooked kernel elongation is a unique feature of basmati type rice and an important quality criterion for that market type.

Embryo. The embryo is the small plant contained within a mature seed.

Essentially all the physiological and morphological characteristics. A plant having essentially all the physiological and morphological characteristics means a plant having the physiological and morphological characteristics of the cultivar that are otherwise present when compared in the same environment, other than an occasional variant trait that might arise during backcrossing, direct introduction of a transgene or genetic modification.

$F_\#$. The "F" symbol denotes the filial generation, and the # is the generation number, such as $F_1$, $F_2$, $F_3$, etc.

Final viscosity. Viscosity at the end of the test or cold paste.

Gene. As used herein, "gene" refers to a unit of inheritance corresponding to DNA or RNA that code for a type of protein or for an RNA chain that has a function in the organism.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce or delete the genetic material may include mutation breeding, genome editing, RNA interference, gene silencing, backcross conversion, genetic transformation, single and multiple gene conversion, and/or direct gene transfer.

Genome editing. A type of genetic engineering in which DNA is inserted, replaced, modified or removed from a genome using artificially engineered nucleases or other targeted changes using homologous recombination. Examples include but are not limited to use of zinc finger nucleases (ZFNs), TAL effector nucleases (TALENs), meganucleases, CRISPR/Cas9, and other CRISPR related technologies. (Ma et. al., *Molecular Plant*, 9:961-974 (2016); Belhaj et. al., *Current Opinion in Biotechnology*, 32:76-84 (2015)).

Genotype. Refers to the genetic constitution of a cell or organism.

Grain length (L). Length of a rice grain is measured in millimeters.

Grain width (W). Width of a rice grain is measured in millimeters.

Grain yield. Grain yield is measured in pounds per acre and at 14.0% moisture. Grain yield of rice is determined by the number of panicles per unit area, the number of fertile florets per panicle, and grain weight per floret.

Haploid. A cell or organism having one set of the two sets of chromosomes in a diploid.

Harvest moisture. The percent of moisture of the grain when harvested.

Head rice. Unbroken kernels of milled rice.

Hot paste viscosity. Viscosity measure of rice flour/water slurry after being heated to 95EC. Lower values indicate softer and stickier cooking types of rice.

Length/Width (L/W) ratio. This ratio is determined by dividing the average length (L) by the average width (W).

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A defined segment of DNA. A locus confers one or more traits such as, for example, male sterility, herbicide resistance trait, insect resistance, disease resistance, and improved yield. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging resistance (also called Straw strength). Lodging is measured as a subjective rating and is percentage of the plant stems leaning or fallen completely to the ground before harvest. Visual scoring where 0%=all plants standing to 100%=all plant in plot are laying flat on the soil surface. Lodged plants are difficult to harvest and reduce yield and grain quality.

Milling yield. Milling yield is the total amount of milled rice (whole and broken kernels) recovered after removal of hulls, bran, and germ by milling and head-rice yield, the total amount of whole kernels recovered after milling. Values are expressed as weight percentage of the original paddy or rough rice sample that was milled. For example, a milling yield of 65/70 is a sample of 100 grams of rough rice that produced 65 grams of head rice and 70 grams of total milled rice.

Multiple gene converted (Conversion). Multiple gene converted (conversion) includes plants developed by a plant breeding technique called backcrossing wherein essentially all of the desired morphological and physiological characteristics of a variety are recovered, while retaining two or more genes transferred into the variety via crossing and backcrossing. The term can also refer to the introduction of multiple genes through genetic engineering techniques known in the art.

Nucleic acid. An acidic, chainlike biological macromolecule consisting of multiple repeat units of phosphoric acid, sugar and purine and pyrimidine bases.

Nutraceutical. Refers to a food or food product that provides health and or medical benefits, including the prevention and treatment of disease. Such products may range from isolated nutrients, dietary supplements and specific diets to genetically engineered foods, herbal products, and processed foods such as cereals, soups and beverages.

1000 Grain wt. The weight of 1000 rice grains as measured in grams. It can be for paddy, brown or milled rice.

Pasting temperature. The pasting temperature, which provides an indication of the minimum temperature required to cook a given sample, can have implications for the stability of other components in a formula and also indicate energy costs.

Pedigree. Refers to the lineage or genealogical descent of a plant.

Pedigree distance. Relationship among generations based on their ancestral links as evidenced in pedigrees. May be measured by the distance of the pedigree from a given starting point in the ancestry.

Percent identity. Percent identity as used herein refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Peak viscosity. The maximum viscosity attained during heating when a standardized instrument-specific protocol is applied to a defined rice flour-water slurry.

Plant. As used herein, the term "plant" includes reference to an immature or mature whole plant, including a plant from which seed, grain, or anthers have been removed. Seed or embryo that will produce the plant is also considered to be the plant.

Plant height. Plant height measured in centimeters or inches is taken from soil surface to the tip of the extended panicle at harvest.

Plant parts. As used herein, the term "plant parts" (or a rice plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Progeny. As used herein, includes an $F_1$ rice plant produced from the cross of two rice plants where at least one plant includes rice cultivar M-211 and progeny further includes, but is not limited to, subsequent $F_2$, $F_3$, $F_4$, $F_5$, $F_6$, $F_7$, $F_5$, $F_9$, and $F_{10}$ generational crosses with the recurrent parental line.

Quantitative Trait Loci (QTL). Quantitative trait loci (QTL) refer to genetic loci that control to some degree numerically representable traits that are usually continuously distributed.

RVA viscosity. Rapid Visco Analyzer is a widely used laboratory instrument to examine paste viscosity, or thickening ability of milled rice during the cooking process.

RVU. The RVA scale is measured in RVUs. This is the native viscosity unit of the RVA. 1 RVU is equivalent to 12 CP. CP equals "centipoises" which equals unit of viscosity (kg s$^{-1}$ m$^{-1}$) and 1 kg s$^{-1}$ m$^{-1}$ equals 1000 centipoises.

Regeneration. Regeneration refers to the development of a plant from tissue culture.

Seedling vigor. Seedling vigor refers to the ability of the seedling to emerge rapidly through the soil or water after planting. It is frequently measured by visual observation field test and assigned a relative score.

Setback. Setback 1 is the final viscosity minus trough viscosity. Setback 2 is the final viscosity minus peak viscosity and is what is most commonly referred to for rice quality testing.

Single gene converted (Conversion). Single gene converted (conversion), also known as coisogenic plants, refers to plants which are developed by a plant breeding technique called backcrossing wherein essentially all of the desired morphological and physiological characteristics of a variety are recovered in addition to the single gene transferred into the variety via the backcrossing technique or via genetic engineering.

Stem rot. Is caused by the fungus *Sclerotium oryzae* Cattaneo (=*Magnaporthe salvinii*). It produces sheath and stem lesions that can reduce yield and grain quality. California varieties are generally rated between 4.5 and 7.5 on a scale of 0 to 10.

Texture score. A relative subjective score used by the breeder in evaluating cooked rice samples. A score of 4 being most sticky and a score of 2 being the least sticky.

Trough viscosity. The minimum viscosity after the peak, normally occurring when the sample starts to cool.

Breeding History of Rice Cultivar M-211 and Summary of Test Results

Rice cultivar M-211 is a very high-yielding, early-maturing, semi-dwarf, temperate *Japonica*, conventional medium-grain rice developed using the pedigree breeding method. It was selected from a cross designated R34424 made during summer of 2007 at the Rice Experiment Station (RES), Biggs, Calif. The pedigree designation of M-211 is M-206/4/M-203/Kiara397//M-205/3/87P1309//M-401/M-203.

M-206 (U.S. Pat. No. 6,911,589) is a high yielding, glabrous, early maturing Calrose variety released by RES in 2003 and widely adapted in rice growing areas in California. Kiara 397 or Kirara 397 is a premium quality, short grain, semi-dwarf rice variety developed in Hokkaido in 1980. It is cold tolerant during booting stage and has good tolerance to leaf and panicle blast. M-205 (U.S. Pat. No. 6,492,582) is a glabrous, high yielding, early maturing Calrose-type medium grain variety released by RES in 2005 and adapted in warmer areas. M-401, which is a semi-dwarf mutant of Terso, is a late maturing medium grain with premium quality released in 1981. M-203 is photoperiod insensitive and an early maturing semi-dwarf medium grain mutant of M-401 developed and released by RES in 1988. M-206, M-205, and M-401 are still being grown in commercial production in California.

Rice cultivar M-211 was tested as experimental 12Y2175 and included in the University of California Cooperative Extension (UCCE) Statewide (SW) Yield Tests—Early Group in 2013 and 2014 (13Y105, 14Y84) as preliminary entry. In 2015 and 2016, M-211 was evaluated in both the SW Yield Tests—Early and Intermediate-Late group experiments. Advanced line M-211 was further evaluated in the SW Yield Test in the Very Early, Early, and Intermediate-Late experiments for yield and adaptation in all rice growing areas of California starting in 2017-2019. In total, the M-211 entry was evaluated in 55 SW Yield Test experiments from 2013 to 2019.

The average grain yield of M-211 in the 2017-2019 SW test averaged 9,712 lb/acre compared to 9,196 and 9,129 lb/acre for M-209 (U.S. Pat. No. 9,693,520) and M-206, respectively. The overall yield advantage of M-211 over both M-209 and M-206 was 6%.

Rice cultivar M-211 has similar seedling vigor (4.8) to M-206 and M-209. Rice cultivar M-211 is 2 cm and 3 cm taller than M-206 and M-209, respectively. On average, M-211 flowered 1 day later than M-209 and 6 days later than M-206. In terms of lodging during maturity, M-211 is more lodging resistant than M-206 with an average percent lodging of 26% compared to 40% of M-206.

Rice cultivar M-211 has shown uniformity and stability as described in the following variety description information. It has been self-pollinated a sufficient number of generations with careful attention to uniformity of plant type. Headrow purification (panicle-to-a-row) was performed from 2016 to 2018 under isolation in a water-seeded field. In 2019, Foundation seed was produced on 5.49 acres at RES. In the purification process, rows that appear to be unstable, had obvious differences in maturity, height, vigor or lodging of plants within a row, or had off-shaped kernels, and grain defects, were discarded. Panicles were collected from selected rows and visually evaluated and selected to compose the next cycle of the headrow purification process. Leaf tissues from each of the rows were collected for DNA fingerprinting using the microsatellites (SSR) markers to further confirm purity.

Rice cultivar M-211 has the following morphologic and other characteristics (based primarily on data collected in California).

TABLE 1

VARIETY DESCRIPTION INFORMATION

Grain type: Medium
Days to maturity (50% heading): 89
Culm:

Angle (degrees from perpendicular after flowering): Erect (less than 30°)
Length (soil level to top of extended panicle on main stem): 102.0 cm
Height class: Medium
Internode color (after flowering): Green
Strength (lodging resistance): Moderately strong (most plants leaning)
Flag leaf (at maturity):

Length: 30.0 cm
Width: 1.5 cm
Pubescence: Glabrous
Leaf angle (after heading): Erect
Blade color (at heading): Dark green
Basal leaf sheath color (at heading): Green
Ligule:

Length (from base of collar to the tip, at late vegetative stage): 17.0 mm
Color (late vegetative stage): White
Shape: Acute to acuminate
Collar color (late vegetative stage): Pale green
Auricle color (late vegetative stage): Pale green
Panicle:

Length: 22.0 cm
Type: Intermediate
Secondary branching: Light
Exertion (near maturity): 100% exerted
Shattering (at maturity): Low (less than 5%)
Threshability: Intermediate
Grain (spikelet):

Awns (after full heading): Absent
Apiculus color (at maturity): Straw
Apiculus color (after full heading): Straw
Stigma color: White
Lemma and palea color (at maturity): Straw
Lemma and palea pubescence: Hairs on lemma keel
Spikelet sterility (at maturity): Highly fertile (>90%)
Grain (seed):

Seed coat color: Light brown
Endosperm type: Nonglutinous (nonwaxy)
Endosperm translucency: Clear
Endosperm chalkiness: Small (<10%)
Scent: Nonscented
Shape class (length/width ratio):

Paddy: Medium (2.3:1 to 3.3:1)

Length: 8.38 mm
Width: 3.42 mm
L/W ratio: 2.44
1000 Grains: 31.5 g
Brown: Short (2.1:1 to 3.31:1)

Length: 6.33 mm
Width: 3.00 mm
L/W ratio: 2.11
1000 Grains: 25.2 g
Milled: Medium (2.0:1 to 3.3:1)

Length: 5.98 mm
Width: 2.92 mm

TABLE 1-continued

VARIETY DESCRIPTION INFORMATION

L/W ratio: 2.04
1000 Grains: 23.6 g
Milling quality (% hulls): 20.0
Milling yield (% whole kernel (head) rice to rough rice): 61/67
% Protein (brown): 5.7
% Amylose: 14.4
Alkali spreading value: 7
Gelatinization temperature type: Low amylographic paste viscosity
Amylographic paste viscosity (RVA measured in RVU):

Peak: 240
Hot paste: 128
Cooled paste: 225
Setback: −14
Resistance to low temperature:

Germination and seedling vigor: Medium
Flowering (spikelet fertility): High
Seedling vigor not related to low temperature: High
Disease resistance:

Rice blast (*Pyricularia oryzae*): Susceptible to races IB1 and IG1 in California
Aggregate sheath spot (*Rhizoctonia oryzae-sativae*): Moderately susceptible
Stem rot (*Sclerotium oryzae*): Intermediate
Insect resistance: None This invention also is directed to methods for producing a rice plant by crossing a first parent rice plant with a second parent rice plant wherein either the first or second parent rice plant is a rice plant of the line M-211. Further, both first and second parent rice plants can come from the rice cultivar M-211. Still further, this invention also is directed to methods for producing a rice cultivar M-211-derived rice plant by crossing rice cultivar M-211 with a second rice plant and growing the progeny seed, and repeating the crossing and growing steps with the rice cultivar M-211-derived plant from 0 to 7 times. Thus, any such methods using the rice cultivar M-211 are part of this invention: selfing, backcrosses, hybrid production, crosses to populations, and the like. All plants produced using rice cultivar M-211 as a parent are within the scope of this invention, including plants derived from rice cultivar M-211. Advantageously, the rice cultivar is used in crosses with other, different, rice cultivars to produce first generation ($F_1$) rice seeds and plants with superior characteristics.

It should be understood that the cultivar can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

Further Embodiments of the Invention

Rice in general is an important and valuable vegetable crop. Thus, a continuing goal of rice plant breeders is to develop stable, high yielding rice cultivars that are agronomically sound. To accomplish this goal, the rice breeder must select and develop rice plants with traits that result in superior cultivars.

Plant breeding techniques known in the art and used in a rice plant breeding program include, but are not limited to, pedigree breeding, recurrent selection, mass selection, single or multiple-seed descent, bulk selection, backcrossing, open pollination breeding, restriction fragment length polymorphism enhanced selection, genetic marker enhanced selection, making double haploids, and transformation. Often combinations of these techniques are used. The development of rice varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Using Rice Cultivar M-211 to Develop Other Rice Varieties

This invention also is directed to methods for producing a rice plant by crossing a first parent rice plant with a second parent rice plant wherein the first or second parent rice plant is a rice plant of cultivar M-211. Further, both first and second parent rice plants can come from rice cultivar M-211. Also provided are methods for producing a rice plant having substantially all of the morphological and physiological characteristics of cultivar M-211, by crossing a first parent rice plant with a second parent rice plant wherein the first and/or the second parent rice plant is a plant having substantially all of the morphological and physiological characteristics of cultivar M-211 set forth in Table 1, as determined at the 5% significance level when grown in the same environmental conditions. The other parent may be any rice plant, such as a rice plant that is part of a synthetic or natural population. Thus, any such methods using rice cultivar M-211 are part of this invention: selfing, backcrosses, hybrid production, crosses to populations, and the like. All plants produced using rice cultivar M-211 as at least one parent are within the scope of this invention, including those developed from cultivars derived from rice cultivar M-211.

The cultivar of the invention can also be used for transformation where exogenous genes are introduced and expressed by the cultivar of the invention. Genetic variants created either through traditional breeding methods using rice cultivar M-211 or through transformation of cultivar M-211 by any of a number of protocols known to those of skill in the art are intended to be within the scope of this invention.

The following describes breeding methods that may be used with rice cultivar M-211 in the development of further rice plants. One such embodiment is a method for developing a progeny rice plant in a rice plant breeding program comprising: obtaining the rice plant, or a part thereof, of cultivar M-211, utilizing said plant or plant part as a source of breeding material, and selecting a rice cultivar M-211 progeny plant with molecular markers in common with cultivar M-211 and/or with morphological and/or physiological characteristics selected from the characteristics listed in Table 1. Breeding steps that may be used in the rice plant breeding program include, but are not limited to, pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of rice cultivar M-211 progeny rice plants, comprising crossing cultivar M-211 with another rice plant, thereby producing a population of rice plants, which, on average, derive 50% of their alleles from rice cultivar M-211. A plant of this population may be selected and repeatedly selfed or sibbed with a rice cultivar resulting from these successive filial generations. One embodiment of this invention is the rice cultivar produced by this method and that has obtained at least 50% of its alleles from rice cultivar M-211.

Progeny of rice cultivar M-211 may also be characterized through their filial relationship with rice cultivar M-211, as for example, being within a certain number of breeding crosses of rice cultivar M-211. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice cultivar M-211 and its progeny. For example, progeny produced by the methods described herein may be within 1, 2, 3, 4 or 5 breeding crosses of rice cultivar M-211.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes rice cultivar M-211 progeny rice plants comprising a combination of at least two cultivar M-211 traits selected from the group consisting of those listed in Table 1 or the cultivar M-211 combination of traits listed in the Detailed Description of the Invention, so that said progeny rice plant is not significantly different for said traits than rice cultivar M-211 as determined at the 5% significance level when grown in the same environmental conditions. Using techniques described herein, molecular markers may be used to identify said progeny plant as a rice cultivar M-211 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

The goal of rice plant breeding is to develop new, unique, and superior rice cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level and the cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. Therefore, two breeders will never develop the same line, or even very similar lines, having the same rice traits.

Pedigree breeding is used commonly for the improvement of self-pollinating crops or inbred lines of cross-pollinating crops. Pedigree breeding starts with the crossing of two genotypes, such as rice cultivar M-211 or a rice variety having all of the morphological and physiological characteristics of M-211, and another rice variety having one or more desirable characteristics that is lacking or which complements rice cultivar M-211. If the two original parents do not provide all the desired characteristics, other sources can be included in the breeding population. In the pedigree method, superior plants are selfed and selected in successive filial generations. In the succeeding filial generations, the heterozygous condition gives way to the homozygous allele condition as a result of inbreeding. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. In some examples, 1, 2, 3, 4, 5, 6, 7, 8, 9, 10, or more generations of selfing and selection are practiced. After a sufficient amount of inbreeding, successive filial generations will serve to increase seed of the developed variety. Preferably, the developed variety comprises homozygous alleles at about 95% or more of its loci.

In addition to being used to create backcross conversion populations, backcrossing can also be used in combination with pedigree breeding. As discussed previously, backcrossing can be used to transfer one or more specifically desirable traits from one variety (the donor parent) to a developed variety (the recurrent parent), which has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a rice variety may be crossed with another variety to produce a first generation progeny plant. The first generation progeny plant may then be backcrossed to one of its parent varieties to create a $F_1BC_1$. Progeny are selfed and selected so that the newly developed variety has many of the attributes of the recurrent parent and yet several of the desired attributes of the donor parent. This approach leverages the value and strengths of both parents for use in new rice varieties.

Therefore, in some examples a method of making a backcross conversion of rice cultivar M-211, comprising the steps of crossing a plant of rice cultivar M-211 or a rice variety having all of the morphological and physiological characteristics of M-211 with a donor plant possessing a desired trait to introduce the desired trait, selecting an $F_1$ progeny plant containing the desired trait, and backcrossing the selected $F_1$ progeny plant to a plant of rice cultivar M-211 are provided. This method may further comprise the step of obtaining a molecular marker profile of rice cultivar M-211 and using the molecular marker profile to select for a progeny plant with the desired trait and the molecular marker profile of M-211. The molecular marker profile can comprise information from one or more markers. In one example the desired trait is a mutant gene or transgene present in the donor parent. In another example, the desired trait is a native trait in the donor parent.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population, will be represented by a progeny when generation advance is completed.

Mutation breeding is another method of introducing new traits into rice varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993. In addition, mutations created in other rice plants may be used to produce a backcross conversion of rice cultivar M-211 that comprises such mutation.

Selection of rice plants for breeding is not necessarily dependent on the phenotype of a plant and instead can be based on genetic investigations. For example, one may utilize a suitable genetic marker which is closely associated with a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay which is able to identify the relative presence or absence of a trait of interest in a plant may also be useful for breeding purposes. Procedures for marker assisted selection applicable to the breeding of rice are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Isozyme Electrophoresis, Restriction Fragment Length Polymorphisms (RFLPs), Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), Simple Sequence Repeats (SSRs), and Single Nucleotide Polymorphisms (SNPs) (Wang et al., Science, 280:1077-1082, 1998).

The production of double haploids can also be used for the development of homozygous varieties in a breeding program. Double haploids are produced by the doubling of a set of chromosomes from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Descriptions of other breeding methods that are commonly used for different traits and crops can be found in one of several reference books (e.g., Allard, "Principles of plant breeding," John Wiley & Sons, NY, University of California, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses," 2d Ed., Manograph 16:249, 1987; Fehr, "Principles of cultivar development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., Corn and Improvement, 5th ed., 2006).

Genotypic Profile of M-211 and Progeny

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, single nucleotide polymorphisms (SNPs), or genome-wide evaluations such as genotyping-by-sequencing (GBS). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety. Favorable genotypes and or marker profiles, optionally associated with a trait of interest, may be identified by one or more methodologies.

In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

The invention further provides a method of determining the genotype of a plant of rice cultivar M-211, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of rice cultivar M-211.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

In some examples, a plant, a plant part, or a seed of rice cultivar M-211 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., Theor. Appl. Genet., 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein, but may include any type of marker and marker profile which provides a means of distinguishing varieties. In addition to being used for identification of rice cultivar M-211, a hybrid produced through the use of M-211, and the identification or verification of pedigree for progeny plants produced through the use of M-211, a genetic marker profile is also useful in developing a gene conversion of M-211.

Rice DNA molecular marker linkage maps have been rapidly constructed and widely implemented in genetic studies such as in Zhu, J. H., et al. (1999) "Toward rice genome scanning by map-based AFLP fingerprinting" Mol. Gene Genetics. 261(1):184-195; Cheng, Z., et al (2001) "Toward a cytological characterization of the rice genome" Genome Research. 11(12):2133-2141; Ahn, S., et al. (1993) "Comparative linkage maps of the rice and maize genomes" Proc. Natl. Acad. Sci. USA. 90(17):7980-7984; and Kao, F. I., et al. (2006) "An integrated map of *Oryza sativa* L. chromosome 5" Theor. Appl. Genet. 112(5):891-902. Sequences and PCR conditions of SSR Loci in rice as well as the most current genetic map may be found in Rice-BLAST and the TIGR Rice Genome Annotation on the World Wide Web.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

The SSR profile of rice cultivar M-211 can be used to identify plants comprising rice cultivar M-211 as a parent, since such plants will comprise the same homozygous alleles as rice cultivar M-211. Because the rice variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the Fiprogeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of rice cultivar M-211 in their development, such as rice cultivar M-211 comprising a gene conversion, backcross conversion, transgene, or genetic sterility factor, may be identified by having a molecular marker profile with a high percent identity to rice cultivar M-211. Such a percent identity might be 95%, 96%, 97%, 98%, 99%, 99.5%, or 99.9% identical to rice cultivar M-211.

The SSR profile of rice cultivar M-211 can also be used to identify essentially derived varieties and other progeny varieties developed from the use of rice cultivar M-211, as well as cells and other plant parts thereof. Such plants may be developed using the markers identified in WO 00/31964, U.S. Pat. Nos. 6,162,967, and 7,288,386. Progeny plants and plant parts produced using rice cultivar M-211 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from rice cultivar M-211, as measured by either percent identity or percent similarity. Such progeny may be further characterized as being within a pedigree distance of rice cultivar M-211, such as within 1, 2, 3, 4, or 5 or less cross-pollinations to a rice plant other than rice cultivar M-211 or a plant that has rice cultivar M-211 as a progenitor. Unique molecular profiles may be identified with other molecular tools such as SNPs and RFLPs.

While determining the genotypic profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Molecular data from M-211 may be used in a plant breeding process. Nucleic acids may be isolated from a seed of M-211 or from a plant, plant part, or cell produced by growing a seed of M-211, or from a seed of M-211 with a gene conversion, or from a plant, plant part, or cell of M-211 with a gene conversion. One or more polymorphisms may be isolated from the nucleic acids. A plant having one or more of the identified polymorphisms may be selected and used in a plant breeding method to produce another plant.

Introduction of a New Trait or Locus into Rice Cultivar M-211

Cultivar M-211 represents a new base genetic variety into which a new gene, locus or trait may be introgressed. Backcrossing and direct transformation represent two important methods that can be used to accomplish such an introgression.

Single or Multiple Gene (Locus) Conversions

When the term "rice plant" is used in the context of the present invention, this also includes any single or multiple gene or locus conversions of that variety. The term "single locus converted plant" or "single gene converted plant" refers to those rice plants which are developed by back-crossing or genetic engineering, wherein essentially all of the desired morphological and physiological characteristics of a variety are recovered in addition to the one or more genes transferred into the variety via the backcrossing technique or genetic engineering. Backcrossing methods can be used with the present invention to improve or introduce a characteristic into the variety.

A backcross conversion of rice cultivar M-211 occurs when DNA sequences are introduced through backcrossing (Hallauer, et al., "Corn Breeding," *Corn and Corn Improvements*, No. 18, pp. 463-481 (1988)), with rice cultivar M-211 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, *Proceedings Symposium of the Analysis of Molecular Data*, Crop Science Society of America, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., *Corn and Corn Improvement, Sprague and Dudley*, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety.

A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in rice cultivar M-211 comprises crossing rice cultivar M-211 plants grown from rice cultivar M-211 seed with plants of another rice variety that comprise the desired trait, gene or locus, selecting $F_1$ progeny plants that comprise the desired trait, gene or locus to produce selected $F_1$ progeny plants, crossing the selected progeny plants with the rice cultivar M-211 plants to produce backcross progeny plants, selecting for backcross progeny plants that have the desired trait, gene or locus and the morphological characteristics of rice cultivar M-211 to produce selected backcross progeny plants, and backcrossing to rice cultivar M-211 two or more times in succession to produce selected third or higher backcross progeny plants that comprise said trait, gene or locus. The modified rice cultivar M-211 may be further characterized as having the physiological and morphological characteristics of rice cultivar M-211 listed in Table 1 as determined at the 5% significance level when grown in the same environmental conditions and/or may be characterized by percent similarity or identity to rice cultivar M-211 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny rice seed by adding a step at the end of the process that comprises crossing rice cultivar M-211 with the introgressed trait or locus with a different rice plant and harvesting the resultant first generation progeny rice seed.

Methods for Genetic Engineering of Rice

With the advent of molecular biological techniques that have allowed the isolation and characterization of genes that encode specific protein products, scientists in the field of plant biology developed a strong interest in engineering the genome of plants (genetic engineering) to contain and express foreign genes, or additional, or modified versions of native, or endogenous genes (perhaps driven by different promoters) in order to alter the traits of a plant in a specific manner. Plants altered by genetic engineering are often referred to as 'genetically modified'. Any DNA sequences, whether from a different species or from the same species, which are introduced into the genome using transformation and/or various breeding methods, are referred to herein collectively as "transgenes." Over the last fifteen to twenty years several methods for producing transgenic plants have been developed, and the present invention, in particular embodiments, also relates to transformed versions of the claimed cultivar.

Vectors used for the transformation of rice cells are not limited so long as the vector can express an inserted DNA in the cells. For example, vectors comprising promoters for constitutive gene expression in rice cells (e.g., cauliflower mosaic virus 35S promoter) and promoters inducible by exogenous stimuli can be used. Examples of suitable vectors include pBI binary vector. The "rice cell" into which the vector is to be introduced includes various forms of rice cells, such as cultured cell suspensions, protoplasts, leaf sections, and callus. A vector can be introduced into rice cells by known methods, such as the polyethylene glycol method, polycation method, electroporation, *Agrobacterium*-mediated transfer, particle bombardment and direct DNA uptake by protoplasts. See, e.g., Pang et al. (The Plant J., 9, 899-909, 1996).

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,563,055 (Townsend and Thomas), issued Oct. 8, 1996.

*Agrobacterium*-mediated transfer is a widely applicable system for introducing gene loci into plant cells, including rice. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio. Tech.*, 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563,055). For example, U.S. Pat. No. 5,349,124 describes a method of transforming rice plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in rice having resistance to such insects.

B. Direct Gene Transfer:

Several methods of plant transformation, collectively referred to as direct gene transfer, have been developed as an alternative to *Agrobacterium*-mediated transformation. A generally applicable method for delivering transforming DNA segments to plant cells is microprojectile-mediated transformation, or microprojectile bombardment. In this method, particles are coated with nucleic acids and delivered into cells by a propelling force. Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol Plant*, 7:206 (1990); Klein, et al., *Bio/technology*, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO 1*, 4:2731 (1985); Christou, et al., *PNAS*, 84:3962 (1987). Direct uptake of DNA into protoplasts using $CaCl_2$) precipitation, calcium phosphate precipitation, polyethylene glycol treatment, polyvinyl alcohol, or poly-L-ornithine has also been reported. See, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335: 454, 1988; Hain, et al., *Mol. Gen. Genet.*, 199:161, 1985 and Draper, et al., *Plant Cell Physiol.* 23:451, 1982.

Electroporation of protoplasts and whole cells and tissues has also been described. Donn, et al., In Abstracts of VIIth International Congress on Plant Cell and Tissue Culture IAPTC, A2-38, p. 53, 1990; D'Halluin, et al., *Plant Cell*, 4:1495-1505, 1992; and Spencer, et al., *Plant Mol. Biol.*, 24:51-61, 1994. Another illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target rice cells.

Transformation of plants and expression of foreign genetic elements is exemplified in Choi et al., *Plant Cell Rep.*, 13: 344-348, 1994 and Ellul et al., *Theor. Appl. Genet.*, 107:462-469, 2003.

Following transformation of rice target tissues, expression of selectable marker genes allows for preferential selection of transformed cells, tissues, and/or plants, using regeneration and selection methods now well known in the art.

The methods described herein for transformation would typically be used for producing a transgenic variety. The transgenic variety could then be crossed, with another (non-transformed or transformed) variety, in order to produce a new transgenic variety. Alternatively, a genetic trait which has been engineered into a particular rice cultivar using the transformation techniques described could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Expression Vectors for Rice Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988). Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS, α-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Rice Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters:

A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT application WO 96/30530.

C. Tissue-Specific or Tissue-Preferred Promoters:

A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990).

Additional Methods for Genetic Engineering of Rice

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety can be generated using "custom" or engineered endonucleases such as meganucleases produced to modify plant genomes (see e.g., WO 2009/114321; Gao et al. (2010) *Plant Journal* 1:176-187). Another site-directed engineering method is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system, as well as similar CRISPR related technologies including but not limited to use of enzymes Cpf1 and Cms1. See e.g., Belhaj et al., (2013), *Plant Methods* 9: 39; The Cas9/guide RNA-based system allows targeted cleavage of genomic DNA guided by a customizable small noncoding RNA in plants (see e.g., WO 2015026883A1, incorporated herein by reference).

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al., *Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, *Curr. Op. Plant Bio.,* 2:109-113 (1999)); target-RNA-specific ribozymes (Haseloff, et al., *Nature,* 334: 585-591 (1988)); hairpin structures (Smith, et al., *Nature,* 407:319-320 (2000); WO 99/53050; WO 98/53083); MicroRNA (Aukerman & Sakai, *Plant Cell,* 15:2730-2741 (2003)); ribozymes (Steinecke, et al., *EMBO J.,* 11:1525 (1992);

Perriman, et al., *Antisense Res. Dev.*, 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

A genetic map can be generated that identifies the approximate chromosomal location of an integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, *Methods in Plant Molecular Biology and Biotechnology*, pp. 269-284 (CRC Press, Boca Raton, 1993).

Wang et al. discuss "Large Scale Identification, Mapping and Genotyping of Single-Nucleotide Polymorphisms in the Human Genome", *Science* (1998) 280:1077-1082, and similar capabilities are increasingly available for the rice genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

Rice Cultivar M-211 Further Comprising a Transgene

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into rice cultivar M-211. Transgenic variants of rice cultivar M-211 plants, seeds, cells, and parts thereof or derived therefrom are provided. Transgenic variants of M-211 comprise the physiological and morphological characteristics of rice cultivar M-211, such as listed in Table 1 as determined at the 5% significance level when grown in the same environmental conditions, and/or may be characterized or identified by percent similarity or identity to M-211 as determined by SSR or other molecular markers. In some examples, transgenic variants of rice cultivar M-211 are produced by introducing at least one transgene of interest into rice cultivar M-211 by transforming M-211 with a polynucleotide comprising the transgene of interest. In other examples, transgenic variants of rice cultivar M-211 are produced by introducing at least one transgene by introgressing the transgene into rice cultivar M-211 by crossing.

In one example, a process for modifying rice cultivar M-211 with the addition of a desired trait, said process comprising transforming a rice plant of cultivar M-211 with a transgene that confers a desired trait is provided. Therefore, transgenic M-211 rice cells, plants, plant parts, and seeds produced from this process are provided. In some examples one more desired traits may include traits such as sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. The specific gene may be any known in the art or listed herein, including but not limited to a polynucleotide conferring resistance to an ALS-inhibitor herbicide, imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to tipburn, *Fusarium oxysporum, Nasonovia ribisnigri, Sclerotinia sclerotiorum* or other plant pathogens.

Foreign Protein Genes and Agronomic Genes

By means of the present invention, plants can be genetically engineered to express various phenotypes of agronomic interest. Through the transformation of rice, the expression of genes can be altered to enhance disease resistance, insect resistance, herbicide resistance, agronomic, nutritional quality, and other traits. Transformation can also be used to insert DNA sequences which control or help control male-sterility. DNA sequences native to rice, as well as non-native DNA sequences, can be transformed into rice and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Likewise, by means of the present invention, agronomic genes can be expressed in transformed plants. More particularly, plants can be genetically engineered to express various phenotypes of agronomic interest. Exemplary nucleotide sequences and/or native loci that confer at least one trait of interest, which optionally may be conferred or altered by genetic engineering, transformation or introgression of a transformed event include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1, 4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a celery endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. A lettuce mosaic potyvirus (LMV) coat protein gene introduced into rice in order to increase its resistance to LMV infection. See Dinant et al., *Molecular Breeding.* 1997, 3: 1, 75-86.

T. Genes involved in the Systemic Acquired Resistance (SAR) Response and/or the pathogenesis-related genes. Briggs, S., *Current Biology,* 5(2) (1995).

U. Antifungal genes. See Cornelissen and Melchers, *Plant Physiol.,* 101:709-712 (1993); Parijs et al., *Planta* 183:258-264 (1991) and Bushnell et al., *Can. J. of Plant Path.* 20(2):137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes That Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvlshikimate-3-phosphate synthase (EPSPS) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPs which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research.* 1999, 8: 1, 33-44 that discloses *Lactuca sativa* resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.,* 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (PPO; protox) is the target of the PPO-inhibitor class of herbicides; a PPO-inhibitor resistant PPO gene was recently identified in *Amaranthus tuberculatus* (Patzoldt et al., *PNAS,* 103(33):12329-2334, 2006). PPO is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

F. Genes that confer resistance to auxin or synthetic auxin herbicides. For example an aryloxyalkanoate dioxygenase (AAD) gene may confer resistance to arlyoxyalkanoate herbicides, such as 2,4-D, as well as pyridyloxyacetate herbicides, such as described in U.S. Pat. No. 8,283,522, and US2013/0035233. In other examples, a dicamba monooxygenase (DMO) is used to confer resistance to dicamba. Other polynucleotides of interest related to auxin herbicides and/or uses thereof include, for example, the descriptions found in U.S. Pat. Nos. 8,119,380; 7,812,224; 7,884,262; 7,855,326; 7,939,721; 7,105,724; 7,022,896; 8,207,092; US2011/067134; and US2010/0279866. Any of the above listed herbicide genes (1-6) can be introduced into the claimed rice cultivar through a variety of means including, but not limited to, transformation and crossing.

3. Genes That Confer or Contribute to a Value-Added Trait, Such as:

A. Increased iron content of the rice, for example by transforming a plant with a soybean ferritin gene as described in Goto et al., *Acta Horticulturae.* 2000, 521, 101-109.

B. Decreased nitrate content of leaves, for example by transforming a rice with a gene coding for a nitrate reductase. See for example Curtis et al., *Plant Cell Report.* 1999, 18:11, 889-896.

C. Increased sweetness of the rice by transferring a gene coding for monellin that elicits a flavor 100,000 times sweeter than sugar on a molar basis. See Penarrubia et al., *Biotechnology.* 1992, 10:5, 561-564.

D. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

E. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

For additional examples of nuclear male and female sterility systems and genes, see also, U.S. Pat. Nos. 5,859, 341, 6,297,426, 5,478,369, 5,824,524, 5,850,014, and 6,265, 640, all of which are hereby incorporated by reference.

5. Genes that Affect Abiotic Stress Resistance

Genes that affect abiotic stress resistance (including but not limited to flowering, seed development, enhancement of nitrogen utilization efficiency, altered nitrogen responsiveness, drought resistance or tolerance, cold resistance or tolerance, high or low light intensity, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), U.S. Pat. No. 6,713,663 (FT), U.S. Pat. Nos. 6,794, 560, 6,307,126 (GAI), WO 96/14414 (CON), WO 96/38560, WO 01/21822 (VRN1), WO 00/44918 (VRN2), WO 99/49064 (GI), WO 00/46358 (FM), WO 97/29123, WO 99/09174 (D8 and Rht), WO 2004/076638, and WO 004/031349 (transcription factors).

Tissue Culture

Further reproduction of the cultivar can occur by tissue culture and regeneration. Tissue culture of various tissues of plants and regeneration of plants therefrom is well known and widely published. For example, see Teng et al., *HortScience.* 1992, 27:9, 1030-1032 Teng et al., *HortScience.* 1993, 28:6, 669-1671, Zhang et al., *Journal of Genetics and Breeding.* 1992, 46:3, 287-290, Webb et al., *Plant Cell Tissue and Organ Culture.* 1994, 38:1, 77-79, Curtis et al., *Journal of Experimental Botany.* 1994, 45:279, 1441-1449, Nagata et al., *Journal for the American Society for Horticultural Science.* 2000, 125:6, 669-672, Komatsuda, T. et al., *Crop Sci.* 31:333-337 (1991); Stephens, P. A., et al., *Theor. Appl. Genet.* (1991) 82:633-635; Komatsuda, T. et al., *Plant Cell, Tissue and Organ Culture,* 28:103-113 (1992); Dhir, S. et al., *Plant Cell Reports* (1992) 11:285-289; Pandey, P. et al., *Japan J. Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having all of the physiological and morphological characteristics of rice variety M-211.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, hypocotyls, pollen, flowers, seeds, leaves, stems, roots, root tips, pistils, anthers, meristematic cells and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

The present invention contemplates a rice plant regenerated from a tissue culture of a variety (e.g., M-211) or hybrid plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", *Jap. J. Breed.* 33 (Suppl.2), 306-307, illus. 1983. Thus, another aspect of this invention is to provide cells which upon growth and differentiation produce rice plants having the physiological and morphological characteristics of variety M-211.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of corn leaf segments. Thus, it is clear from the literature that the state of the art is such that these methods of obtaining plants are routinely used and have a very high rate of success. Thus, another aspect of this invention is to provide cells which upon growth and differentiation produce rice plants having the physiological and morphological characteristics of rice cultivar M-211.

The utility of rice cultivar M-211 also extends to crosses with other species. Commonly, suitable species will be of the family Graminaceae, and especially of the genera *Zea, Tripsacum, Croix, Schlerachne, Polytoca, Chionachne*, and *Trilobachne*, of the tribe Maydeae.

Uses of Rice Cultivar M-211

The seed of rice cultivar M-211, the plant produced from the cultivar seed, the hybrid rice plant produced from the crossing of the cultivar, hybrid seed, and various parts of the hybrid rice plant and transgenic versions of the foregoing, can be utilized for human food, livestock feed, and as a raw material in industry. As a non-limiting example, rice cultivar M-211 can be used as a commodity plant product for rice, meal, flour, oil, film, packaging, and nutraceutical products.

Tables

Table 2 shows the combined results of the University of California Cooperative Extension Statewide Yield Tests from 2017 to 2019 for rice cultivar M-211 (experimental designation 12Y2175) compared to the medium grain varieties M-209 and M-206. The replicated test plots were 10×20 foot plots and tests were performed in commercial fields at RES in Biggs, Calif., Butte County, Colusa County, Glenn County, San Joaquin County, Sutter County, Yolo County, and Yuba County. Values are averages of entries from tests. Column 1 shows the entry name, column 2 shows the grain yield in pounds per acre (lbs/acre), column 3 shows the percent (%) yield advantage of M-211, column 4 shows the seedling vigor score on a scale of 1-5, column 5 shows the days to 50% heading, column 6 shows the percent (%) lodging, and column 7 shows the plant height in centimeters (cm). Seedling vigor score is a visual score where a score of 1 is poor and a score of 5 is excellent.

TABLE 2

| Entry | Grain Yield (lbs/acre) | % Yield Advantage | Seedling Vigor (1-5) | Days to Heading | Lodging (%) | Plant Height (cm) |
|---|---|---|---|---|---|---|
| M-211 | 9,712 | — | 4.8 | 89 | 26 | 101 |
| M-209 | 9,196 | 6 | 4.8 | 88 | 20 | 98 |
| M-206 | 9,129 | 6 | 4.8 | 83 | 40 | 99 |

As shown in Table 2, rice cultivar M-211 differs from M-209 and M-206 by having a higher grain yield, more days to 50% heading, and taller plant height.

Table 3 shows the agronomic results from the University of California Cooperative Extension Statewide (SW) Yield Tests for 2015 to 2019 for rice cultivar M-211 by location and percent yield advantage in comparison to the M-209 and M-206 varieties. Column 1 shows the test location and year, column 2 shows the seedling vigor score on a scale of 1 to 5, column 3 shows the days to 50% heading, column 4 shows the plant height in centimeters (cm), column 5 shows the percent (%) lodging, column 6 shows the grain yield in pounds per acre (lbs/acre), and column 7 shows the percent (%) yield advantage of M-211 over M-209 and M-206.

TABLE 3

| Location | Seedling Vigor (1-5) | Days to Heading | Plant Height (cm) | Lodging (%) | Grain Yield (lbs/acre) | % Yield Advantage of M-211 over M-209 | % Yield Advantage of M-211 over M-206 |
|---|---|---|---|---|---|---|---|
| Very Early SW, 2017-2019 | | | | | | | |
| Biggs | 4.8 | 82 | 104 | 8 | 10700 | 9 | 17 |
| Yolo | 4.7 | 88 | 100 | 1 | 9580 | 3 | 3 |
| S. Yolo | 4.7 | 99 | 89 | 36 | 7380 | −2 | −7 |
| Sutter | 4.8 | 87 | 93 | 9 | 10070 | 11 | 9 |
| Overall Mean | 4.7 | 89 | 97 | 14 | 9430 | 5 | 6 |
| Early SW, 2015-2019 | | | | | | | |
| Biggs | 4.7 | 82 | 103 | 26 | 10780 | 6 | 11 |
| Colusa | 4.7 | 95 | 105 | 10 | 9770 | 5 | 7 |
| Butte | 4.8 | 91 | 102 | 49 | 9830 | 8 | 5 |
| Yuba | 4.8 | 88 | 102 | 53 | 8930 | 3 | −1 |
| Overall Mean | 4.8 | 89 | 103 | 34 | 9830 | 6 | 6 |
| Intermediate-Late SW, 2016-2019 | | | | | | | |
| Biggs | 4.9 | 81 | 105 | 7 | 10970 | 11 | 14 |
| Butte | 4.8 | 90 | 102 | 47 | 9670 | 7 | 0 |
| Glenn | 4.7 | 92 | 106 | 39 | 8990 | 0 | 8 |
| Overall Mean | 4.8 | 88 | 104 | 31 | 9880 | 6 | 7 |
| Grand Mean | 4.8 | 89 | 101 | 26 | 9710 | 6 | 6 |

As shown in Table 3, rice cultivar M-211 differs from M-209 and M-206 by having higher grain yield in all but a few tests.

Table 4 shows the grain dimensions and 1000 kernel weight of rice cultivar M-211 compared to the medium grain varieties M-209 and M-206. Samples were collected from the RES in Biggs, Calif. in 2017 to 2019. Column 1 shows the year, column 2 shows the entry name, columns 3-5, 6-8, 9, 10, and 12 show the length in millimeters (mm), width in millimeters (mm), and 1000 kernel weight in grams (g) for paddy, brown, and milled rice, respectively, and column 11 shows the length/width (L/W) ratio for the milled rice.

TABLE 4

| | | Paddy Rice | | | Brown Rice | | | Milled Rice | | | |
|---|---|---|---|---|---|---|---|---|---|---|---|
| Year | Entry | Length (mm) | Width (mm) | 1000-seed wt. | Length (mm) | Width (mm) | 1000-seed wt. | Length (mm) | Width (mm) | L/W Ratio | 1000-seed wt. |
| 2017 | M-211 | 8.61 | 3.46 | 31.36 | 6.41 | 3.01 | 26.87 | 5.99 | 2.94 | 2.04 | 24.36 |
|  | M-209 | 8.73 | 3.25 | 30.44 | 6.48 | 2.83 | 25.23 | 6.05 | 2.76 | 2.19 | 23.06 |
|  | M-206 | 8.20 | 3.22 | 28.49 | 6.17 | 2.83 | 24.39 | 5.76 | 2.77 | 2.08 | 21.90 |
| 2018 | M-211 | 8.51 | 3.37 | 31.26 | 6.32 | 2.91 | 25.48 | 5.92 | 2.83 | 2.09 | 23.07 |
|  | M-209 | 8.68 | 3.17 | 30.65 | 6.55 | 2.78 | 25.37 | 6.01 | 2.69 | 2.23 | 22.55 |
|  | M-206 | 8.48 | 3.23 | 29.19 | 6.20 | 2.82 | 24.40 | 5.73 | 2.70 | 2.12 | 21.23 |

TABLE 4-continued

| | | Paddy Rice | | | Brown Rice | | | Milled Rice | | | |
|---|---|---|---|---|---|---|---|---|---|---|---|
| Year | Entry | Length (mm) | Width (mm) | 1000-seed wt. | Length (mm) | Width (mm) | 1000-seed wt. | Length (mm) | Width (mm) | L/W Ratio | 1000-seed wt. |
| 2019 | M-211 | 8.02 | 3.47 | 31.80 | 6.27 | 3.07 | 26.00 | 6.03 | 2.99 | 2.02 | 23.50 |
| | M-209 | 8.28 | 3.26 | 30.70 | 6.42 | 2.83 | 24.40 | 6.15 | 2.75 | 2.24 | 22.30 |
| | M-206 | 8.11 | 3.33 | 30.80 | 6.23 | 2.86 | 24.20 | 6.04 | 2.90 | 2.09 | 22.50 |
| Mean | M-211 | 8.38 | 3.43 | 31.47 | 6.33 | 3.00 | 26.12 | 5.98 | 2.92 | 2.05 | 23.64 |
| | M-209 | 8.56 | 3.23 | 30.60 | 6.48 | 2.81 | 25.00 | 6.07 | 2.73 | 2.22 | 22.64 |
| | M-206 | 8.26 | 3.26 | 29.49 | 6.20 | 2.84 | 24.33 | 5.84 | 2.79 | 2.10 | 21.88 |

As shown in Table 4, the paddy, brown, and milled rice grains of rice cultivar M-211 have larger 1000 seed weight than the other varieties.

Table 5 summarizes the average milling yields of rice cultivars M-211, M-209, and M-206 taken at RES milling plots from 2017 to 2019. Results showed that the head rice yield of M-211 when harvested at 18-22% is 61/67 (head/total) compared to 62/68 of M-209 and 64/69 of M-206. Although the total milled rice is highest at moisture content lower than 18%, the head rice of M-211 is lowest when cut at moistures below 18% compared to the check varieties. Column 1 shows the entry name and columns 2-4 show milling head/total (no. of samples) when harvested below 18%, from 18 to 22%, and above 22% harvest moisture, respectively.

TABLE 5

| | % Moisture Content at Harvest | | |
|---|---|---|---|
| Entry | Less than 18% | 18-22% | More than 22% |
| M-211 | 53/68 (6) | 61/67 (9) | 59/66 (5) |
| M-209 | 59/69 (5) | 62/68 (8) | 60/67 (8) |
| M-206 | 63/71 (2) | 64/69 (12) | 64/69 (10) |

As shown in Table 5, the optimum harvest moisture for best milling yields is between 18 to 22%. M-211 milling yields are less than M-206 and slightly less than M-209.

Table 6 summarizes the test results for RVA, apparent amylose, protein content, and gelatinization temperature type of rice cultivars M-211, M-209, and M-206 conducted by RES, the USDA-ARS Rice Quality Laboratory, and the California Wheat Commission from 2017 to 2019. Column 1 shows year, column 2 shows the entry name, columns 3-8 show the RVA results, column 9 shows the apparent amylose (%), column 10 shows the brown rice protein percent (%), and column 11 shows the gelatinization temperature type.

TABLE 6

| | | RVA | | | | | | Apparent Amylose (%) | Protein (%) (brown rice) | Gel Type |
|---|---|---|---|---|---|---|---|---|---|---|
| Year | Entry | Peak | Trough | Break down | Final Visc. | Setback | Pasting Temp | | | |
| 2017 | M-211 | 225 | 131 | 94 | 218 | −7 | 95 | 14.7 | 5.7 | Low |
| | M-209 | 232 | 130 | 101 | 222 | −10 | 95 | 14.5 | 5.2 | Low |
| | M-206 | 270 | 143 | 127 | 242 | −28 | 94 | 14.6 | 7.4 | Low |
| 2018 | M-211 | 237 | 122 | 116 | 228 | −9 | 95 | 14.0 | 5.7 | Low |
| | M-209 | 261 | 125 | 136 | 230 | −30 | 93 | 12.1 | 5.6 | Low |
| | M-206 | 269 | 130 | 139 | 243 | −26 | 94 | 12.9 | 6.5 | Low |
| 2019 | M-211 | 256 | 133 | 124 | 230 | −26 | 90 | 14.4 | 6.0 | Low |
| | M-209 | 283 | 144 | 139 | 247 | −37 | 88 | 13.3 | 6.4 | Low |
| | M-206 | 297 | 146 | 151 | 253 | −44 | 88 | 14.4 | 6.3 | Low |
| Mean | M-211 | 240 | 128 | 111 | 225 | −14 | 93 | 14.37 | 5.80 | Low |
| | M-209 | 259 | 133 | 125 | 233 | −26 | 92 | 13.31 | 5.73 | Low |
| | M-206 | 279 | 140 | 139 | 246 | −33 | 92 | 13.98 | 6.73 | Low |

As shown in Table 6, the rice grain quality parameters of RVA profile, amylose, protein, and gelatinization temperature type all fall within categories for temperate *japonica* U.S. medium grain Calrose market type rice.

Table 7 summarizes the disease reactions of rice cultivar M-211 to stem rot and blast infections compared to M-209 and M-206. Column 1 shows the variety name, column 2 shows the year, column 3 shows the stem rot score, column 4 shows the year, and column 5 shows the blast score. Reaction to stem rot infection was performed in an inoculated field nursery, while blast resistance screening was conducted in the greenhouse from 2015 to 2017. Severity of disease infection of test entries was scored from 1 to 5 with 5 being highly susceptible and 1 being highly resistant to disease infection.

TABLE 7

| | | Disease Score | | |
|---|---|---|---|---|
| Variety | Year | Stem Rot | Year | Blast |
| M-211 | 2017 | 3.0 | 2015 | 3.50 |
| M-209 | | 3.6 | | 3.58 |
| M-206 | | 5.0 | | 3.48 |
| M-211 | 2018 | 4.1 | 2016 | 3.30 |
| M-209 | | 3.6 | | 3.00 |
| M-206 | | 4.3 | | 3.15 |
| M-211 | 2019 | 4.0 | 2017 | 3.00 |
| M-209 | | 4.5 | | 3.00 |
| M-206 | | 3.0 | | 3.00 |
| M-211 | Mean | 3.70 | Mean | 3.27 |

TABLE 7-continued

| | | Disease Score | | |
|---|---|---|---|---|
| Variety | Year | Stem Rot | Year | Blast |
| M-209 | | 3.92 | | 3.19 |
| M-206 | | 4.11 | | 3.21 |

As shown in Table 7, the results indicate that rice cultivar M-211 is moderately susceptible to both stem rot and blast diseases. In comparison to M-209 and M-206, M-211 is less susceptible to stem rot. M-211 has a similar level of susceptibility to blast infection as M-209 and M-206 based on these results.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the California Cooperative Rice Research Foundation, Inc. proprietary rice cultivar M-211 disclosed above and recited in the appended claims has been made with the American Type Culture Collection (ATCC), 10801 University Boulevard, Manassas, Va. 20110 under the terms of the Budapest Treaty. The date of deposit was Sep. 10, 2020. The deposit of 25 packets of 25 seeds each was taken from the same deposit maintained by California Cooperative Rice Research Foundation, Inc. since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126835. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of rice cultivar M-211, wherein a representative sample of seed of said cultivar has been deposited under ATCC Accession No. PTA-126835.

2. A rice plant, or a plant part thereof, produced by growing the seed of claim 1.

3. A tissue culture of cells or protoplasts produced from the plant of claim 2, wherein said cells or protoplasts of the tissue culture are produced from a plant part selected from the group consisting of leaf, pollen, ovule, embryo, cotyledon, hypocotyl, meristematic cell, root, root tip, pistil, anther, flower, stem, seed, glumes and panicle.

4. A rice plant regenerated from the tissue culture of claim 3, wherein the plant has all of the morphological and physiological characteristics of rice cultivar M-211.

5. A method for producing an $F_1$ hybrid rice seed, wherein the method comprises crossing the plant of claim 2 with a different rice plant and harvesting the resultant $F_1$ hybrid rice seed.

6. An F1 hybrid rice seed produced by the method of claim 5.

7. An F1 hybrid rice plant, or a part thereof, produced by growing said hybrid rice seed of claim 6, wherein the part comprises at least one cell of the rice cultivar M-211.

8. A method of producing an herbicide resistant rice plant, wherein the method comprises transforming the rice plant of claim 2 with a transgene, wherein the transgene confers resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine, benzonitrile, protoporphyrinogen oxidase (PPO)-inhibitor herbicides, and broxynil.

9. An herbicide resistant rice plant produced by the method of claim 8.

10. A method of producing a pest or insect resistant rice plant, wherein the method comprises transforming the rice plant of claim 2 with a transgene that confers pest or insect resistance.

11. A pest or insect resistant rice plant produced by the method of claim 10.

12. The rice plant of claim 11, wherein the transgene encodes a *Bacillus thuringiensis* endotoxin.

13. A method of producing a disease resistant rice plant, wherein the method comprises transforming the rice plant of claim 2 with a transgene that confers disease resistance.

14. A disease resistant rice plant produced by the method of claim 13.

15. A method of producing a rice plant with modified fatty acid metabolism or modified carbohydrate metabolism, wherein the method comprises transforming the rice plant of claim 2 with a transgene encoding a protein selected from the group consisting of fructosyltransferase, levansucrase, alpha-amylase, invertase and starch branching enzyme or DNA encoding an antisense of stearyl-ACP desaturase.

16. A rice plant having modified fatty acid metabolism or modified carbohydrate metabolism produced by the method of claim 15.

17. A method of introducing a desired trait into rice cultivar M-211, wherein the method comprises:
(a) crossing a M-211 plant, wherein a representative sample of seed was deposited under ATCC Accession No. PTA-126835, with a plant of another rice cultivar that comprises a desired trait to produce progeny plants, wherein the desired trait is selected from the group consisting of male sterility, herbicide resistance, pest or insect resistance, abiotic stress tolerance, modified fatty acid metabolism, modified carbohydrate metabolism, enhanced nutritional quality, modified protein content, enhanced plant quality and resistance to bacterial disease, fungal disease or viral disease;
(b) selecting one or more progeny plants that have the desired trait;
(c) backcrossing the selected progeny plants with the M-211 plants to produce backcross progeny plants;
(d) selecting for backcross progeny plants that have the desired trait; and
(e) repeating steps (c) and (d) two or more times to produce selected third or higher backcross progeny plants that comprise the desired trait.

18. A plant produced by the method of claim 17, wherein the plant has the desired trait and otherwise all of the physiological and morphological characteristics of rice cultivar M-211.

19. The plant of claim 18, wherein the desired trait is herbicide resistance and the resistance is conferred to an herbicide selected from the group consisting of glyphosate, sulfonylurea, imidazolinone, dicamba, glufosinate, phenoxy proprionic acid, L-phosphinothricin, cyclohexone, cyclohexanedione, triazine, benzonitrile, protoporphyrinogen oxidase (PPO)-inhibitor herbicides and broxynil.

20. The plant of claim 18, wherein the desired trait is insect resistance and the insect resistance is conferred by a transgene encoding a *Bacillus thuringiensis* endotoxin.

21. The plant of claim 18, wherein the desired trait is modified fatty acid metabolism or modified carbohydrate metabolism and said desired trait is conferred by a nucleic acid encoding a protein selected from the group consisting of fructosyltransferase, levansucrase, alpha-amylase, invertase and starch branching enzyme or DNA encoding an antisense of stearyl-ACP desaturase.

22. The plant of claim 18, wherein the desired trait is abiotic stress tolerance and said desired trait modifies tolerance to drought, flooding, salinity, or temperature change.

23. The method of claim 5, wherein the method further comprises:
(a) crossing a plant grown from said $F_1$ hybrid rice seed with itself or a different rice plant to produce a seed of a progeny plant of a subsequent generation;
(b) growing a progeny plant of a subsequent generation from said seed of a progeny plant of a subsequent generation and crossing the progeny plant of a subsequent generation with itself or a second plant to produce a progeny plant of a further subsequent generation; and
(c) repeating steps (a) and (b) using said progeny plant of a further subsequent generation from step (b) in place of the plant grown from said $F_1$ hybrid rice seed in step (a), wherein steps (a) and (b) are repeated with sufficient inbreeding to produce an inbred rice plant derived from the rice cultivar M-211.

24. The method of claim 23, further comprising crossing said inbred rice plant derived from the rice cultivar M-211 with a plant of a different genotype to produce a seed of a hybrid rice plant derived from the rice cultivar M-211.

25. A method of introducing the head rice stability trait of rice cultivar M-211 into another rice cultivar, wherein the method comprises crossing a M-211 plant, wherein a representative sample of seed is deposited under ATCC Accession No. PTA-126835, with a plant of another rice cultivar and selecting for progeny plants that have head rice stability.

26. A method of producing a genetically modified rice plant, wherein the method comprises mutation, gene conversion, genome editing, RNA interference or gene silencing of the plant of claim 2.

27. A genetically modified rice plant produced by the method of claim 26, wherein said plant comprises said mutation, gene conversion, genome edit, RNA interference or silenced gene and otherwise comprises all of the physiological and morphological characteristics of rice cultivar M-211.

28. A method of producing a commodity plant product, comprising obtaining the plant of claim 2, or a part thereof, and producing the commodity plant product from said plant or plant part thereof, wherein said commodity plant product is selected from the group consisting of rice, meal, flour, oil, film, packaging, and nutraceutical product.

\* \* \* \* \*